United States Patent [19]

Utagawa et al.

[11] 4,371,613

[45] Feb. 1, 1983

[54] METHOD FOR PRODUCING PURINE ARABINOSIDES

[75] Inventors: Takashi Utagawa, Kawasaki; Takeshi Miyoshi, Fijisawa; Hirokazu Morisawa, Kawasaki; Akihiro Yamazaki, Yokosuka; Fumihiro Yoshinaga, Fujisawa; Koji Mitsugi, Yokohama, all of Japan

[73] Assignee: Ajinomoto Company Incorporated, Tokyo, Japan

[21] Appl. No.: 930,046

[22] Filed: Aug. 1, 1978

[30] Foreign Application Priority Data

Aug. 10, 1977 [JP] Japan .................................. 52/95766
Dec. 28, 1977 [JP] Japan .................................. 52/158738
Jan. 11, 1978 [JP] Japan .................................. 53/1802
Jul. 11, 1978 [JP] Japan .................................. 53/84196
Jul. 18, 1978 [JP] Japan .................................. 53/87288

[51] Int. Cl.$^3$ ........................ C12P 19/40; C12P 19/32

[52] U.S. Cl. ......................................... 435/88; 435/92
[58] Field of Search .................. 195/28 N; 435/88, 92

[56] References Cited

U.S. PATENT DOCUMENTS 3,269,917  8/1966  Imada et al. ...................... 195/28 N
4,055,718 10/1977  Baker ................................ 195/28 N

*Primary Examiner*—Alvin E. Tanenholtz
*Attorney, Agent, or Firm*—Olbon, Fisher, Spivak, McClelland & Maier

[57] ABSTRACT

Purine-arabinosides and a method for making purine-arabinosides are disclosed. The method comprises contacting an arabinose donor and a purine source in the presence of an effective amount of enzyme produced by a bacterium and capable of transarabinosylation from the arabinose donor to the purine source, whereby a 9-(β-D-arabinofuranosyl)-purine is produced.

12 Claims, 6 Drawing Figures

METHOD FOR PRODUCING PURINE ARABINOSIDES

BACKGROUND OF THE INVENTION

1. Field of the Invention

This invention relates to a method for producing purine-arabinosides, particularly by an enzymatic process.

2. Description of the Prior Art

Purine-arabinosides (9-(β-D-arabinofuranosyl)-purines) have potential utility as agricultural chemicals or medicinal agents. For example, it has been reported that adenine arabinoside, one of the purine arabinosides has been used successfully to treat several diseases caused by the herpes virus including chickenpox and shingles.

As to known methods for producing the purine arabinosides, several chemically synthetic methods have been proposed, (J. Org. Chem. 27, 3274, (1962); J. Org. Chem. 28, 3004 (1963); J. Org. Chem, 32, (1976); Tetrahedron Letters 1970, 4673; and Japanese Published Examined Patent Application No. 7271/1972). It is further reported that adenine arabinoside is produced when Streptomyces antibioticus is cultured in conventional culture media (Japanese Published Examined Patent Application No. 41558/1972).

SUMMARY OF THE INVENTION

It has been found that purine arabinosides are produced in aqueous reaction media from an arabinose donor such as uracil arabinoside or D-arabinofuranose-1-phosphate and a purine-source such as adenine, hypoxanthine, adenosine and adenosine-5'-monophosphate by the action of an enzyme produced by various bacteria.

A commercially applicable method for producing purine arabinosides has now been provided by (a) holding at a temperature in the range from 40° to 70° C. in an aqueous medium an arabinose donor selected from the group consisting of D-arabinofuranose-1-phosphate, and the compound having Formula I on a nucleotide thereof; and a purine source selected from the group consisting of unsubstituted or 2,6 and/or 8-substituted purine and its ribofuranoside, ribofuranotide, deoxyribofuranoside or deoxyribofuranotide, in the presence of an effective amount of an enzyme produced by a bacterium and capable of transarabinosylation from the arabinose donor to the unsubstituted or 2,6 and/or 8-substituted purine of the purine source, whereby the β-D-arabinofuranosyl radical is attached to the 9-position of the unsubstituted or 2,6 and/or 8-substituted purine; and (b) recovering the produced 9-(β-D-arabinofuranosyl)-unsubstituted or 2,6 and/or 8-substituted purine.

Formula I

X represents O, S or NH;
Y represents OH, $NH_2$, SH or SR(R is a lower alkyl group); and
Z represents H, halogen, $NO_2$, $CH_3$ or $CH_2OH$.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

The arabinose donors of this invention are D-arabinofuranose-1-phosphates of, the compounds of formula I, or the phosphate of the compound showing formula I. The specimens of the arabinose donors are shown in the Examples of this invention.

The purine sources of this invention are unsubstituted or 2,6 and/or 8-substituted purine and its ribofuranoside, deoxyribofuranoside or deoxyribofuranotide. The 2,6 and/or 8-substituted purine used in this invention as the purine source can be prepared by the following method: the Ribofuranoside of a 2,6 and/or 8-substituted purine is held with the enzyme of this invention in an aqueous medium containing 0.1 M $KH_2PO_4$ at 60° C. for 24 hours. When the 2,6 and/or 8 substituted purine of the originally used 2,6 and/or 8-substituted purine ribofuranoside, and D-ribofuranose-1-phosphate or D-ribose derived from the above ribofuranoside are produced in the aqueous medium, the 2,6 and/or 8-substituted purine can then be used as the purine source.

The substituents of the 2,6 and/or 8-substituted purines are, for example, halogen, hydroxyl, amino, lower alkyl, alkoxyl, aryl, aralkyl, mercapto, alkylamino, alkylmercapto, alkylsulfonyl, alkylsulfenyl, carboxyl, alkoxycarbonyl, cyano, and nitro radicals.

The D-arabinofuranose of the arabinose donor is enzymatically transferred to and attached to 9-position of the unsubstituted or 2,6/or 8-substituted purine of the purine source. Thus, the product of this invention is 9-($\beta$-D-arabinofuranosyl)-unsubstituted or 2,6 and/or 8-substituted purine.

The bacterial enzyme capable of transarabinosylation from the arabinose donor to unsubstituted or 2,6 and/or 8-substituted purine of the purine source is produced mainly in the bacterial cells and is present to a small extent in the supernatant of the culture liquids. The bacteria capable of producing the enzyme belong, as found so far, to the genera Pseudomonas, Flavobacterium, Achromobacter, Salmonella, Citrobacter, Escherichia, Klebsiella, Enterobacter, Aeromonas, Serratia, Erwinia, Proteus, Xanthomonas, and Bacterium.

Specimens of the bacteria are:

| | |
|---|---|
| *Pseudomonas stutzeri* | NRRL B-11346 (FERM-P 4170), |
| *Flavobacterium rhenanum* | NRRL B-11343 (CCM 298), |
| *Flavobacterium acidoficum* | ATCC 8366, |
| *Flavobacterium proteus* | ATCC 12841, |
| *Achromobacter lacticum* | NRRL B-11340 (CCM 69), |
| *Salmonella typhimirim* | NRRL B-11347 (FERM-P3735), |
| *Citrobacter freundii* | ATCC 8090, |
| *Citrobacter freundii* | ATCC 6750, |
| (*Citrobacter intermedium*) | |
| *Escherichia coli* | ATCC 9637, |
| *Escherichia aurescens* | ATCC 12814, |
| *Klebsiella pneumoniae* | ATCC 9621, |
| (*Enterobacter aerogenes*) | |
| *Serratia liquefaciens* | ATCC 14460, |
| (*Enterobacter liquefaciens*) | |
| *Enterobacter aerogenes* | ATCC 13048, |
| *Aeromonas punctata* | ATCC 11163, |
| *Aeromonas salmonicida* | ATCC 14174, |
| *Serratia marcescens* | IFO 3048, |
| *Erwinia carotovora* | NRRL B-11342 (CCM 872), |
| *Erwinia amylovora* | NRRL B-11341 (CCM 1017), |
| *Erwinia herbicola* | ATCC 14537, |
| *Proteus vulgaris* | NRRL B-11345 (FERM-P3394), |
| *Proteus rettgeri* | NRRL B-11344 (FERM-P3395), |
| *Bacterium cadaveris* | IFO 3731, and |
| *Xanthomonas citri* | NRRL B-11348 (FERM-P3396). |

In order to produce the enzyme using the bacteria as mentioned above, the bacteria are cultured in or on conventional culture media. The culture media contain conventional carbon sources, nitrogen sources, inorganic ions, and when required minor organic nutrients such as vitamins and amino acid. Usual manner can be applied to culture the bacteria in the conventional media, that is, the bacteria are cultured aerobically preferably at a pH of a range from 4 to 9 and a temperature of a range from 25° to 40° C.

As the enzyme source, intact cells, culture liquids containing the cells are used preferably. Additionally, cells dried with acetone, freeze-dried cells, homogenized cells, cells treated with supersonic waves, cells treated with toluene, surfactants or lysozyme are employed giving desirable results. Moreover protein fractions having the enzyme activity capable of transarabinosylation from the arabinose donor to unsubstituted or 2,6 and/or 8-substituted purine of the purine source can be used preferably as the enzyme source. It is expected that there is more than one enzyme participating in the production of the purine arabinosides.

The production of the purine arabinosides can be carried out by holding in the culture media of the bacteria the purine source and the arabinose donor. In this case, the arabinose donor and purine source are added into the culture media after the bacteria has grown sufficiently, and thereafter the temperature is maintained at 40° C. to 70° C. The production of the purine arabinoside can be also carried out by contacting the purine source and arabinose-donor with the cells or the enzyme sources as mentioned above in aqueous reaction media other than culture media. Thus, in this invention, "aqueous medium" means culture medium or reaction medium (reaction mixture). The reaction media are maintained preferably at a temperature from 40° C. to 70° C., and at a pH of 4 to 10 for 5 to 100 hours.

The reaction temperature (40° C. to 70° C.) of this invention is specific in the point that the temperature is higher than the ordinarily enzyme reaction temperature, and it is critical.

The purine arabinosides produced in the culture media or the reaction media can be recovered by conventional manners such as ion exchange method or crystallization technique.

Having generally described this invention, a further understanding can be obtained by reference to certain specific examples which are provided herein for purposes of illustration only and are not intended to be limiting unless otherwise specified.

EXAMPLE 1

An aqueous culture medium of pH 7.2 was prepared which contained, per deciliter, 0.5 g yeast extract, 1.0 g peptone, 0.5 g bouillon, and 0.5 g NaCl. Five ml batches of the aqueous culture medium were placed in test tubes, and heated to sterilize. Each one loopful inocculum of the bacteria listed in Table 1 was transferred into each batch of the aqueous culture medium. Cultivation was carried out at 30° C. for 36 hours with shaking. The cells produced in the culture liquid were collected by centrifugation and washed with physiological saline. The cells thus obtained (50 mg(wet)/ml) were suspended in samples of 0.05 M phosphate buffer of pH 7.0, and 0.5 ml of the suspension of the cells was mixed with 0.5 ml of reaction mixture of pH 7.5 containing 0.5 g/dl uracil arabinoside, 0.2 g/dl hypoxanthine and 50 mg/dl $KH_2PO_4$. Each mixture was held at 60° C. for 15 hours, and thereafter heated to 100° C. for 5 minutes.

Each product in the reaction mixture was identified as 9-$\beta$-D-arabinofuranosylhypoxanthine (hypoxanthine arabinoside) by high speed liquid chromatography, and the amounts of the hypoxanthine arabinoside in the reaction mixture were determined by high speed liquid chromatography, and are shown in Table 1.

TABLE 1

| microorganism used | hypoxanthine arabinoside accumulated mg/dl |
|---|---|
| NRRL B-11343 | 3.7 |
| ATCC 8366 | 6.6 |
| ATCC 12841 | 6.7 |
| NRRL B-11340 | 5.7 |
| NRRL B-11347 | 7.5 |
| ATCC 8090 | 11.3 |
| ATCC 6750 | 13.2 |
| ATCC 9637 | 10.5 |
| ATCC 12814 | 17.0 |
| ATCC 9621 | 126.0 |
| ATCC 14460 | 17.0 |
| ATCC 14174 | 36.0 |
| ATCC 11163 | 4.1 |
| IFO 3048 | 23.0 |
| NRRL B-11342 | 14.0 |
| NRRL B-11341 | 18.0 |
| ATCC 14537 | 21.0 |
| NRRL B-11345 | 9.6 |
| NRRL B-11344 | 2.4 |
| NRRL B-11348 | 11.0 |
| IFO 3731 | 12.0 |
| NRRL B-11346 | 7.5 |

TABLE 1-continued

| microorganism used | hypoxanthine arabinoside accumulated mg/dl |
|---|---|
| ATCC 13048 | 55.7 |

EXAMPLE 2

In the method shown in Example 1, adenine was substituted for hypoxanthine, and the amounts of adenine arabinoside shown in Table 2 were produced in the reaction mixture.

EXAMPLE 3

In the method shown in Example 1, cytosine arabinoside was substituted for uracil arabinoside, and the amounts of hypoxanthine arabinoside shown in Table 3 were produced in the reaction mixture.

EXAMPLE 4

In the method shown in Example 1, adenine riboside-5'-monophosphate was substituted for hypoxanthine, and the amounts of adenine arabinoside shown in Table 4 were accumulated in the reaction mixture.

TABLE 2

| microorganism used | adenine arabinoside accumulated mg/dl |
|---|---|
| NRRL B-11343 | 4.5 |
| ATCC 8366 | 8.2 |
| ATCC 12841 | 8.0 |
| NRRL B-11340 | 6.5 |
| NRRL B-11347 | 8.6 |
| ATCC 8090 | 13.3 |
| ATCC 6750 | 15.0 |
| ATCC 9637 | 10.6 |
| ATCC 12814 | 18.8 |
| ATCC 9621 | 132.0 |
| ATCC 14460 | 26.0 |
| ATCC 14174 | 41.0 |
| ATCC 11163 | 18.5 |
| IFO 3048 | 32.6 |
| NRRL B-11342 | 20.5 |
| NRRL B-11341 | 22.5 |
| ATCC 14537 | 31.5 |
| NRRL B-11345 | 26.3 |
| NRRL B-11344 | 28.6 |
| NRRL B-11348 | 13.5 |
| IFO 3731 | 21.2 |
| NRRL B-11346 | 8.6 |
| ATCC 13048 | 71.8 |

TABLE 3

| microorganism used | hypoxanthine arabinoside accumulated mg/dl |
|---|---|
| NRRL B-11343 | 4.2 |
| ATCC 8366 | 5.5 |
| ATCC 12841 | 8.2 |
| NRRL B-11340 | 2.6 |
| NRRL B-11347 | 4.8 |
| ATCC 8090 | 6.5 |
| ATCC 6750 | 10.3 |
| ATCC 9637 | 6.3 |
| ATCC 12814 | 3.6 |
| ATCC 9621 | 82.1 |
| ATCC 14460 | 15.0 |
| ATCC 14174 | 20.5 |
| ATCC 11163 | 0.8 |
| IFO 3048 | 13.6 |
| NRRL B-11342 | 2.6 |
| NRRL B-11341 | 8.7 |
| ATCC 14537 | 15.0 |
| NRRL B-11345 | 8.1 |
| NRRL B-11344 | 0.5 |
| NRRL B-11348 | 0.8 |

TABLE 3-continued

| microorganism used | hypoxanthine arabinoside accumulated mg/dl |
|---|---|
| IFO 3731 | 10.6 |
| NRRL B-11346 | 3.2 |
| ATCC 13048 | 40.2 |

TABLE 4

| microorganism used | adenine arabinoside accumulated mg/dl |
|---|---|
| NRRL B-11343 | 3.8 |
| ATCC 8366 | 5.6 |
| ATCC 12841 | 7.2 |
| NRRL B-11340 | 3.5 |
| NRRL B-11347 | 8.3 |
| ATCC 8090 | 10.2 |
| ATCC 6750 | 8.6 |
| ATCC 9637 | 5.5 |
| ATCC 12814 | 6.9 |
| ATCC 9621 | 82.3 |
| ATCC 14460 | 13.5 |
| ATCC 14174 | 25.5 |
| ATCC 11163 | 9.6 |
| IFO 3048 | 21.5 |
| NRRL B-11342 | 15.5 |
| NRRL B-11341 | 11.5 |
| ATCC 14537 | 18.3 |
| NRRL B-11345 | 12.6 |
| NRRL B-11344 | 15.8 |
| NRRL B-11348 | 8.3 |
| IFO 3731 | 14.5 |
| NRRL B-11346 | 8.5 |
| ATCC 13048 | 49.6 |

EXAMPLE 5

A hundred ml batches of the aqueous culture medium shown in Example 1 were placed in a 500 ml shaking flask and heated to sterilize. Klebsiella pneumoniae ATCC 9621 was inocculated in the aqueous culture medium and cultured at 30° C. for 36 hours with shaking. Cells produced in the resultant culture liquid were collected by centrifugation, and 30 g (wet) of the cells was put into 1 l of the reaction mixture of pH 7.0 containing 1.5 g 2-methylhypoxanthine, 7.3 g uracil arabinoside and 3.4 g $KH_2PO_4$. The reaction mixture was held at 60° C. for 36 hours.

Cells were removed from the reaction mixture by centrifugation, the supernatant was passed through cation exchange resin ("Amberlite CG-120"), and the resin was washed with 0.1 N ammonium acetate (pH 6.8). After eluting with 0.1 N ammonium hydroxide, the eluate was evaporated and cooled, and 710 mg crystals were obtained.

The crystalline product was determined as 9-($\beta$-D-arabinofuranosyl)-2-methylhypoxanthine(2-methyl-hypoxanthine arabinoside) by its NMR spectrum, UV spectrum, IR spectrum, and elemental analysis.

Elemental analysis: Calculated; C:46.8%, H:5.0%, N:19.8%. Found; C:46.5%, H:5.1%, N:19.5%.

Figure 1:
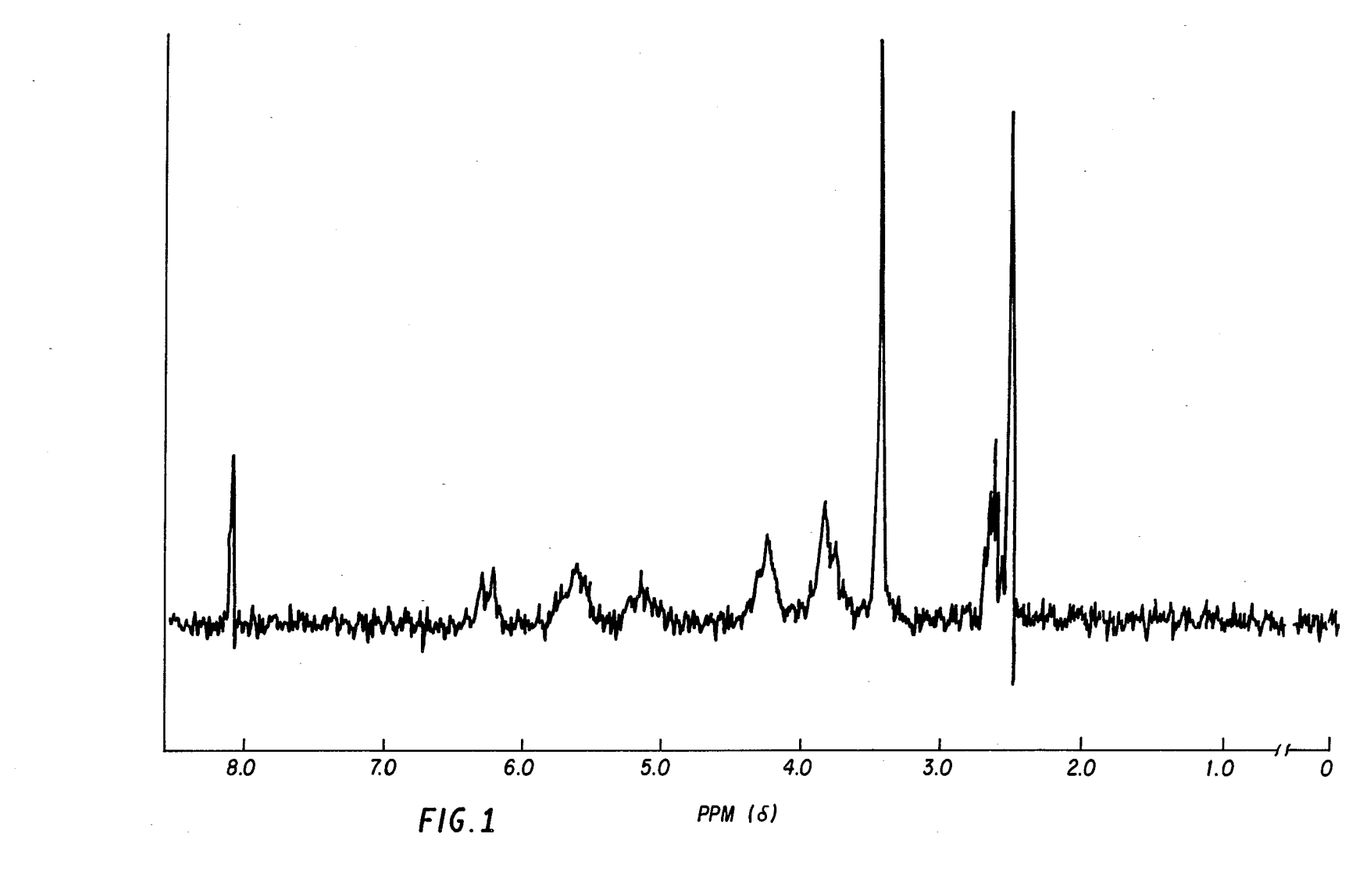
FIG. 1 is the NMR spectrum of the crystalline product obtained in Example 5.
Figure 2:
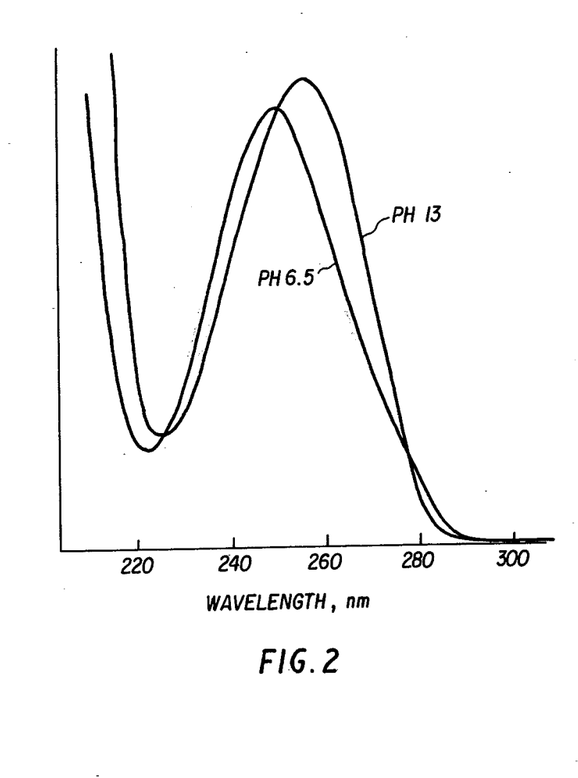
FIG. 2 is the ultra-violet spectrum of the product obtained in Example 5.
Figure 3:
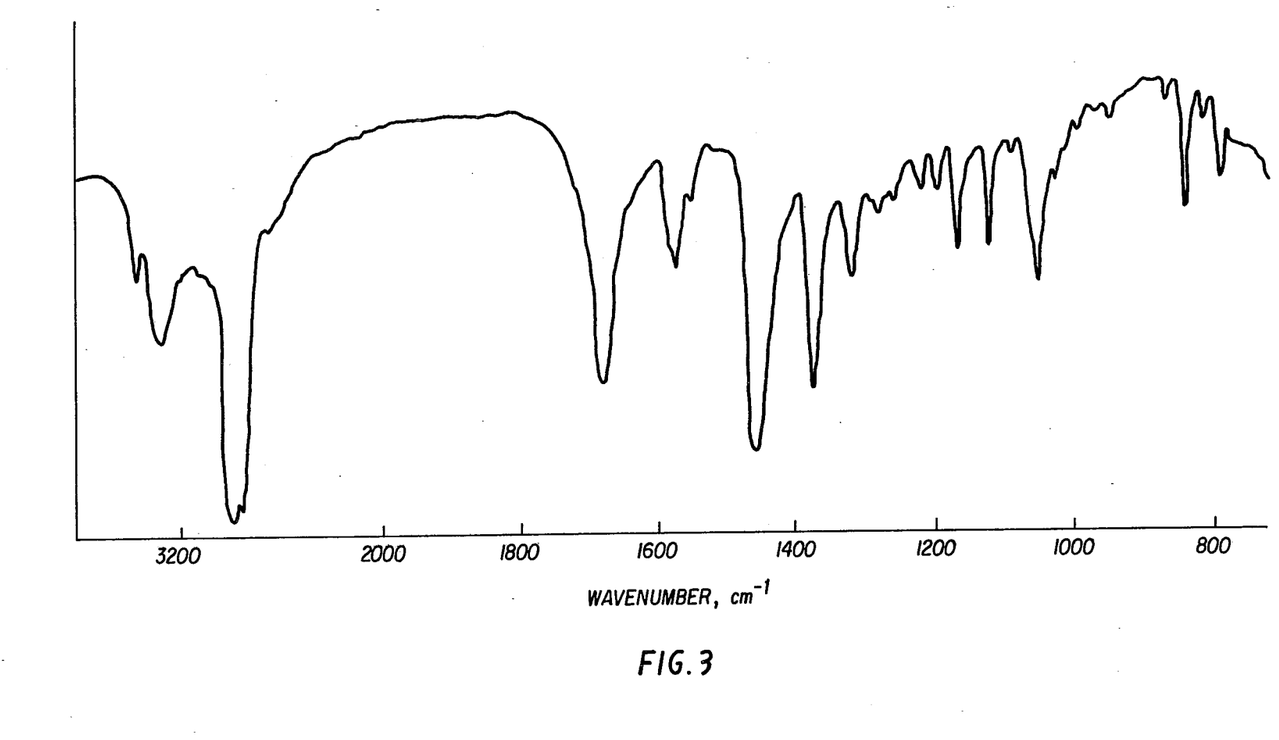
FIG. 3 is the IR spectrum of the product obtained in Example 5.

NMR spectrum: shown in FIG. 1.
UV spectrum: shown in FIG. 2.
IR spectrum: shown in FIG. 3.

EXAMPLE 6

Thirty grams of the cells obtained in Example 4 were put into 1 l of reaction mixture containing 1.7 g 2-chloro-hypoxanthine, 7.3 g uracil arabinoside, and 3.4 g $KH_2PO_4$, and the reaction mixture was held at 60° C. for 36 hours. After removing the cells from the reaction mixture, the supernatant was passed through anion exchange resin ("Dowex IX4"), and the resin was washed with 0.1 N ammonium acetate of pH 6.8. After eluting with 0.1 N ammonium acetate of pH 4.0, the eluate was evaporated, and charged on "Sephadex G-10", and developed with water. The eluate portions showing the first of two peaks peak of UV absorption of the two was collected, evaporated and cooled. Then, 326 mg crystals were obtained.

The crystalline product was determined as 9-($\beta$-D-arabinofuranosy)-2-chlorohypoxanthine(2-chlorohypoxanthine arabinoside) by its NMR spectrum, UV spectrum, IR spectrum, elemental analysis and Beilstein test.

Elemental analysis: Calculated; C:39.68, H:3.66, N:18.51. Found; C:39.42, H:3.72, N:18.25.

Figure 4:
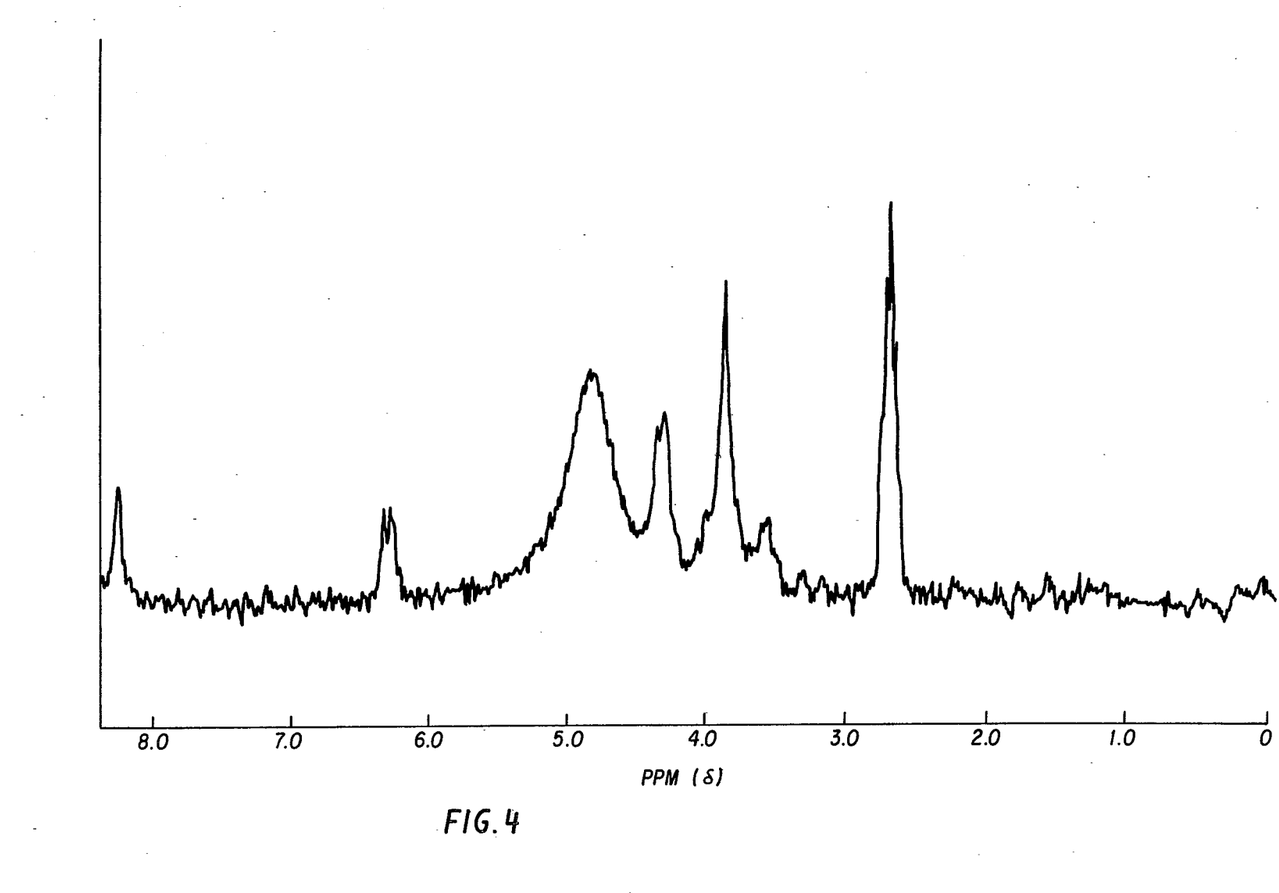
FIG. 4 is the NMR spectrum of the crystalline product obtained from Example 6.
Figure 5:
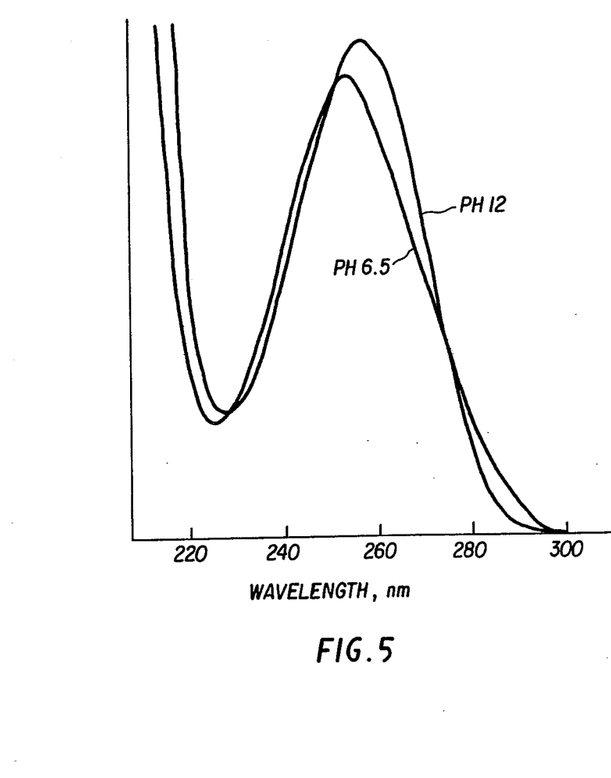
FIG. 5 is the UV spectrum of the product obtained from Example 6.
Figure 6:
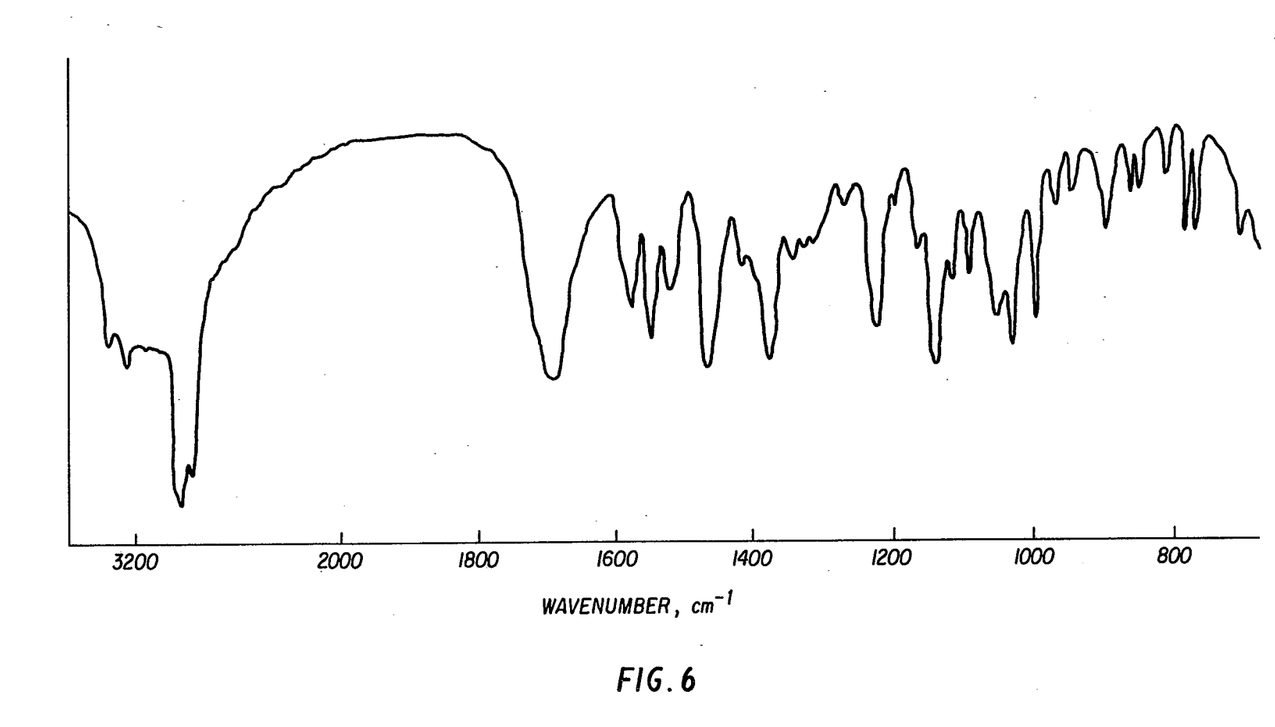
FIG. 6 is the IR spectrum of the product obtained from Example 6.

NMR spectrum: shown in FIG. 4
UV spectrum: shown in FIG. 5
IR spectrum: shown in FIG. 6
Beilstein test: positive (green)

EXAMPLE 7

In the method shown in Example 1, 2-methylhypoxanthine or 2-chlorohypoxanthine was substituted for hypoxanthine, and the amounts of 2-methylhypoxanthine arabinoside or 2-chlorohypoxanthine arabinoside shown in Table 5 were accumulated in the reaction mixture.

EXAMPLE 8

In the method shown in Example 1, 0.2 g/dl hypoxanthine was replaced with 0.4 g/dl inosine, and the amounts of hypoxanthine arabinoside shown in Table 6 were produced in the reaction mixture.

EXAMPLE 9

A hundred ml of the aqueous culture medium shown in Example 1 was placed in a 500 ml shaking flask, heated to sterilize, and inoculated with Aeromonas salmonicida ATCC 14174. Cultivation was carried out at 30° C. for 36 hours with shaking.

Cells produced in the resultant culture liquid were collected by centrifigation, and 2.0 g (wet weight) of the cells were put into 100 ml reaction mixture of pH 7.5 containing 100 mg hypoxanthine, 300 mg uracil arabinoside and 50 mg $KH_2PO_4$. The reaction mixture was then held at 60° C. for 15 hours.

Twenty five mg of crystals of hypoxanthine arabinoside were obtained from the reaction mixture.

TABLE 5

| microorganism | 2-methylhypoxanthine arabinoside accumulated mg/dl | 2-chlorohypoxanthine arabinoside accumulated mg/dl |
|---|---|---|
| NRRL B-11343 | 2.1 | 0.5 |
| ATCC 8366 | 3.4 | 0.8 |
| ATCC 12841 | 4.0 | 2.1 |
| NRRL B-11340 | 5.5 | 2.5 |
| NRRL B-11347 | 4.8 | 2.8 |
| ATCC 8090 | 8.7 | 3.6 |
| ATCC 6750 | 9.5 | 8.2 |
| ATCC 9637 | 4.7 | 5.1 |
| ATCC 12814 | 12.0 | 10.5 |
| ATCC 9621 | 80.5 | 51.6 |
| ATCC 14460 | 18.5 | 11.3 |
| ATCC 14174 | 21.6 | 10.0 |
| ATCC 11163 | 0.8 | 0.05 |
| IFO 3048 | 15.4 | 10.8 |
| NRRL B-11342 | 2.5 | 0.1 |
| NRRL B-11341 | 12.0 | 10.5 |
| ATCC 14537 | 15.5 | 12.1 |
| NRRL B-11345 | 0.6 | 0.05 |
| NRRL B-11344 | 8.2 | 0.5 |
| NRRL B-11348 | 12.5 | 0.8 |
| IFO 3731 | 21.6 | 2.1 |
| NRRL B-11346 | 15.3 | 10.3 |
| ATCC 13048 | 40.2 | 28.7 |

TABLE 6

| microorganism used | hypoxanthine arabinoside accumulated mg/dl |
|---|---|
| NRRL B-11343 | 2.8 |
| ATCC 8366 | 3.6 |
| ATCC 12841 | 5.5 |
| NRRL B-11340 | 4.3 |
| NRRL B-11347 | 6.2 |
| ATCC 8090 | 8.8 |
| ATCC 6750 | 7.4 |
| ATCC 9637 | 1.6 |
| ATCC 12814 | 13.6 |
| ATCC 9621 | 83.3 |
| ATCC 14460 | 6.2 |
| ATCC 14174 | 16.8 |
| ATCC 11163 | 0.9 |
| IFO 3048 | 15.3 |
| NRRL B-11342 | 6.8 |
| NRRL B-11341 | 10.2 |
| ATCC 14537 | 8.9 |
| NRRL B-11345 | 8.5 |
| NRRL B-11344 | 0.8 |
| NRRL B-11348 | 7.2 |
| IFO 3731 | 5.8 |
| NRRL B-11346 | 3.3 |
| ATCC 13048 | 40.4 |

EXAMPLE 10

Klebsiella pneumoniae ATCC 9621 was cultured in the manner shown in Example 9. Cells in the resultant culture liquid were collected by centrifugation, and 2 g (wet weight) of the cells were suspended in 100 ml reaction mixture of pH 7.5 containing 100 mg hypoxanthine, 300 mg cytosine arabinoside, 50 mg $KH_2PO_4$, and the reaction mixture was held at 60° C. for 15 hours.

The cells in the reaction mixture were removed by centrifugation, and a concentrate of the supernatant was passed through anion exchange resin ("Dowex-1" OH form, pH 6.8). After eluting with 0.1 N formic acid of pH 4.0, the eluate was passed through "Sephadex G-10". Eluate (250 ml) obtained by eluting with water was concentrated and the concentrate was added with methanol and cooled to form crystals of the product. After re-crystallization with water, 35 mg purified crystals were obtained.

The crystalline product was identified with authentic hypoxanthine arabinoside by its NMR spectrum, IR spectrum and UV spectrum.

EXAMPLE 11

Klebsiella pneumoniae ATCC 9621 was cultured by the same manner as in Example 9, and cells were collected by centrifugation.

Hypoxanthine in the reaction mixture in Example 9 was replaced with adenine, and the reaction mixture was held at 60° C. for 15 hours. The supernatant of the reaction mixture was concentrated to 20 ml. Upon cooling the concentrate, 80 mg crystals were obtained.

The crystalline product was identified with authentic adenine arabinoside by its NMR spectrum, IR spectrum, and UV spectrum.

EXAMPLE 12

*Erwinia hervicola* ATCC 14537 was cultured by the same manner as in Example 9, and the cells produced were collected by centrifugation.

The cells thus obtained (2 g (wet weight)/dl) were suspended in 100 ml of a reaction mixture of pH 7.5 containing 100 mg/dl adenine, 300 mg/dl cytosine arabinoside and 50 mg $KH_2PO_4$, and held at 60° C. for 15 hours.

After removing the cells from the reaction mixture, the reaction mixture was concentrated to 20 ml, and cooled. The crystals thus obtained were recrystallized with water and 55 mg purified crystals were obtained. The crystalline product was identified with adenine arabinoside by its NMR spectrum, IR spectrum and UV spectrum.

EXAMPLE 13

Cells (5 g (wet)/dl) of *Aeromonas salmonicida* ATCC 14174 were suspended in 100 ml batches of a reaction mixture containing 30 mM cytosine arabinoside, 25 mM $KH_2PO_4$, and 10 mM of one of the purines shown in Table 7. The reaction mixtures were placed in test tubes and held at 60° C. for 15 hours.

Newly formed product having UV absorption in the resultant reaction mixture was separated by liquid chromatography. The eluate of the chromatography was concentrated and added with ethanol, whereby crystals were formed in the eluate.

From NMR spectra and UV spectra of the purified crystalline products, the products were ascertained as the arabinosides of the respective purines used as the starting materials.

Conversion ratio of the purine arabinosides from purine source were determined by measuring molecular extinction coefficient, and are shown in Table 7.

TABLE 7

| Starting material | Product | Conversion ratio (%) |
|---|---|---|
| xanthine | xanthine arabinoside | 15 |
| guanine | guanine arabinoside | 8 |
| purine | purine arabinoside | 23 |
| 6-mercaptopurine | 6-mercaptopurine arabinoside | 8 |
| 2,6-diaminopurine | 2,6-diaminopurine arabinoside | 38 |
| 6-mercaptoguanine | 6-mereaptoguanine arabinoside | 7 |
| 2-methylhypoxanthine | 2-methylhypoxanthine arabinoside | 35 |
| 2-chlorohypoxanthine | 2-chlorohypoxanthine arabinoside | 18 |

EXAMPLE 14

Cells (5 g (wet)/dl) of *Klebsiella pneumoniae* ATCC 9621 were suspended in 100 ml batches of a reaction mixture placed in test tubes, containing 30 mM uracil arabinoside, 25 mM $KH_2PO_4$, and one of the purine sources (10 mM) listed in Table 8, and the reaction mixture was held at 60° C. for 15 hours.

Newly formed product having UV-absorption in the resultant reaction mixture was separated by liquid chromatography. The eluate of the chromatography was concentrated and added to ethanol, whereby crystals were formed in the eluate.

From NMR spectra of the purified crystalline products, the products were ascertained as the arabinoside of the respective purine sources used as starting materials.

Conversion rate of purine arabinosides from the purine sources used was determined by measuring the molecular extinction, coefficient, and are shown in Table 8.

TABLE 8

| Starting material | Product | Conversion ratio (%) |
|---|---|---|
| xanthine | xanthine arabinoside | 65 |
| guanine | guanine arabinoside | 20 |
| purine | purine arabinoside | 36 |
| 6-mercaptopurine | 6-mercaptopurine arabinoside | 8 |
| 2,6-diaminopurine | 2,6-diaminopurine arabinoside | 52 |
| 6-mercaptoguanine | 6-mercaptoguanine arabinoside | 5 |

EXAMPLE 15

In the method shown in Example 5, 2-methylhypoxanthine was replaced with 2-ethylhypoxanthine. The resultant reaction mixture was charged on thin-layer silica-gel, and the chromatogram was developed with water-saturated butanol. The part of Rf 0.4 having absorption at 260 nm on the thin-layer was collected, and suspended in 0.1 NHCl, and silica-gel was removed from the suspension.

When the supernatant of the suspension was made 6 N with HCl and boiled for 10 minutes, orcinol-ferric chloride reaction of the boiled suspension became positive, and 2-ethylhypoxanthine was found in the boiled suspension by paper-chromatography. Thus, it is suggested that 2-ethylhypoxanthine arabinoside was produced in the reaction mixture.

EXAMPLE 16

Cells of *Klebsiella pneumoniae* ATCC 9621 were obtained by the same manner as in Example 9, suspended in 0.5 M phosphate buffer of pH 7.5 to obtain 100 g (wet)/l, and treated with super supersonic.

A hundred ml of a reaction mixture, of pH 7.5 containing 50 ml/dl the supernatant, 500 mg/dl uracil arabinoside-5-monophosphate, 100 mg/dl hypoxanthine and 30 mg/dl $KH_2PO_4$, was held at 60° C. for 15 hours. Then the reaction mixture was centrifuged to remove precipitates, and the supernatant was passed through cation exchange resin ("Chromobead C-2").

Elution was made with 0.3 N formic acid, and the eluate was charged on anion exchange resin ("Dowex 1×4"). Hypoxanthine arabinoside was eluted by gradient elution with ammonium formate of pH 9 to 3 and 8 mg of crystals were obtained from the eluate.

EXAMPLE 17

One ml of a reaction mixture containing, per milliliter, 0.2 ml of the supernatant shown in Example 16. 10 mg uracil arabinoside, 2 mg $KH_2PO_4$, 2 mg of one of the purine sources shown below was held at 60° C. in a test tube for 15 hours, and heated at 100° C. for 5 minutes.

After removing precipitates in the reaction mixture, the reaction mixture was subjected to paper chromatography, and the spot having UV-absorption and having a Rf value different from that of the purine sources used as the starting material was cut, and put into 0.1 N HCl. Then the 0.1 N HCl was made 6 N by adding concentrated HCl after removing filter paper, and boiled for 10 minutes, arabinose was found by an ferric chloride reaction in the boiled 6 NHCl. Thus, it is expected that arabinosides of the following sources used as the starting materials were produced in the reaction mixtures:
- 6-chloropurine
- 2-chlorohypoxanthine
- 2-aminopurine
- 2-methylthiohypoxanthine
- 8-chloroadenine
- 6-mercaptopurine
- 6-methylthiopurine
- 2-amino-6-mercaptopurine
- 6-carboxypurine
- 8-bromoadenine

EXAMPLE 18

In the method shown in Example 16, uracil arabinoside-5'-monophosphate was replaced with cytocine arabinoside-5'-monophosphate. In the resultant reaction mixture, hypoxanthine arabinoside was found.

TABLE 9

| microorganism used | hypoxanthine arabinoside accumulated mg/dl |
|---|---|
| NRRL B-11343 | 2.8 |
| ATCC 8366 | 5.5 |
| ATCC 12841 | 6.3 |
| NRRL B-11340 | 6.0 |
| NRRL B-11347 | 5.2 |
| ATCC 8090 | 8.8 |
| ATCC 6750 | 10.6 |
| ATCC 9637 | 8.5 |
| ATCC 12814 | 12.3 |
| ATCC 9621 | 103.6 |
| ATCC 14460 | 12.5 |
| ATCC 14174 | 29.3 |
| ATCC 11163 | 4.0 |
| IFO 3048 | 24.0 |
| NRRL B-11342 | 15.2 |
| NRRL B-11341 | 17.6 |
| ATCC 14537 | 22.3 |
| NRRL B-11345 | 15.6 |
| NRRL B-11344 | 3.2 |
| NRRL B-11348 | 10.6 |
| IFO 3731 | 18.3 |
| NRRL B-11346 | 8.2 |
| ATCC 13048 | 48.5 |

EXAMPLE 19

In the method shown in Example 1, D-arabinofuranose-1-phosphate was substituted for uracil arabinoside, and the amounts of hypoxanthine arabinoside shown in Table 9 were accumlated in the reaction mixture.

EXAMPLE 20

In the method shown in Example 19, one of the purine sources listed in Table 10 was substituted for hypoxanthine, and newly formed product having UV-absorption in the resultant reaction mixture was separated by preparative high speed liquid chromatography. The eluate of the chromatography was concentrated and added to ethanol, whereby crystals were formed in the eluate. From NMR spectra and UV spectra of the crystalline products, the products were ascertained as the arabinosides of the respective purine sources used as the starting materials.

The conversion ratio of the purine sources used to the purine arabinosides was determined by measuring the molecular extention coefficient and shown in Table 10.

TABLE 10

| Starting material | product | Conversion ratio (%) |
|---|---|---|
| xanthine | xanthine arabinoside | 15 |
| guanine | guanine arabinoside | 8 |
| purine | purine arabinoside | 23 |
| 6-mercaptopurine | 6-mercaptopurine arabinoside | 8 |
| 2,6-diaminopurine | 2,6-diaminopurine arabinoside | 38 |
| 6-mercaptoguanine | 6-mercaptoguanine arabinoside | 7 |
| 2-methylhypoxanthine | 2-methylhypoxanthine arabinoside | 35 |
| 2-chlorohypoxanthine | 2-chlorohypoxanthine arabinoside | 18 |

EXAMPLE 21

*Klebsiella pneumoniae* ATCC 9621 was cultured by the same manner as in Example 9, and the cells produced were collected by centrifugation.

20 mg of the cells obtained were suspended in 1 ml of a reaction mixture of pH 7.0 containing 1.5 mg of adenine. 10 mg of one of the pyrimidine arabinosides listed in Table 11, and 3.4 mg of $KH_2PO_4$, and the reaction mixture was held at 60° C. for 15 hours.

Cells were removed from the reaction mixture by centrifugation. Adenine arabinoside accumulated was identified by high speed liquid chromatography.

TABLE 11

| arabinose donor |
|---|
| 4-thiouracil arabinofuranoside |
| 4-(S-methyl-)thiouracil arabinofuranoside |
| 2-thiouracil arabinofuranoside |
| 5-nitrouracil arabinofuranoside |
| 5-hydroxymethyluracil arabinofuranoside |
| isocytosine arabinofuranoside |
| 5-fluorouracil arabinofuranoside |
| 5-bromouracil arabinofuranoside |
| 5-Iodouracil arabinofuranoside |
| thymine arabinofuranoside |

EXAMPLE 22

In the method shown in Example 11, adenine in the reaction mixture was replaced with 200 mg adenylic acid, and the reaction mixture was held at 60° C. for 15 hours. The supernatant of the reaction mixture was concentrated to 30 ml. Upon cooling the concentrate, 48 mg crystals were obtained. The crystalline product was identified with authentic adenine arabinoside by its NMR spectrum IR spectrum, and UV spectrum.

EXAMPLE 23

In the method shown in Example 11, adenine in the reaction mixture was replaced with 150 mg guanosine, and the reaction mixture was held at 60° C. for 15 hours. The crystals of 2-(β-D-arabinofuranosyl)guanine (guanine arabinoside) (28 mg) were obtained from the supernatant of the resulted reaction mixture.

EXAMPLE 24

In the method shown in Example 13, adenosine, deoxyadenosine, deoxyadenylic acid, guanylic acid, deoxyguanylic acid, xanthosine, deoxyxanthosine, deoxyinosine or deoxyinosinic acid were used in place of hypoxanthine as the purine source. From the above adenine source, adenine arabinoside was formed in the reaction mixture and separated by the usual manner. From the above guanine source, guanine arabinoside was formed. From the above xanthine source, the xanthine arabinoside was formed. From the hypoxanthine source, hypoxanthine arabinoside was formed.

Having now fully described this invention, it will be apparent to one of ordinary skill in the art that many changes and modifications can be made thereto without departing from the spirit or scope of the invention set forth herein.

What is claimed as new and intended to be secured by Letters Patent is:

1. A method for producing purine arabinoside, which comprises:
    (a) holding at a temperature in the range from 40° C. to 70° C. in an aqueous medium in arabinose donor selected from the group consisting of D-arabinofuranose-1-phosphate, the compound of formula I and the phosphate of said compound, and a purine source selected from the group consisting of unsubstituted or 2,6 and/or 8-substituted purine and its ribofuranoside, ribofuranotide, deoxyribofuranoside or deoxyribofuranotide in the presence of an effective amount of enzyme produced by a bacterium and capable of transarabinosylation from the arabinose donor to the unsubstituted or 2,6 and/or 8-substituted purine of the purine source, whereby β-D-arabinofuranosyl radical is attached to the 9-position of the unsubstituted or 2,6 and/or 8-substituted purine; and
    (b) recovering the produced 9-(β-D-arabinofuranosyl)-unsubstituted or 2,6 and/or 8-substituted purine Formula I:

X represents O, S or NH;
Y represents OH, NH$_2$, SH or SR (R is a lower alkyl group); and
Z represents H, halogen, NO$_2$, CH$_3$ or CH$_2$OH.

2. The method of claim 1, wherein the substituents of said 2,6 and/or 8-substituted purine are selected from the group consisting of halogen, hydroxyl, amino, lower alkyl, alkoxyl, aryl, aralkyl, mercapto, alkylamino, alkylmercapto, alkylsulfonyl, alkylsulfenyl, carboxyl, alkoxycarbonyl, nitro and cyano radicals.

3. The method of claim 1, wherein the substituents of 2,6 and/or 8-substituted purine is amino, hydroxyl, and mercapto radical.

4. The method of claim 1, wherein said purine source is selected from the group consisting of adenine, adenosine, deoxyadenosine, deoxyadenylic acid, adenylic acid, hypoxanthine, inosine, deoxyinosine, dexoyinosinic acid, inosinic acid, guanylic acid, xanthine, xanthosine, deoxyxanthosine and xanthylic acid.

5. The method of claim 1, wherein the arabinose donor is 1-β-D-arabinofuranosyl-cytosine or 1-β-D-arabinofuranosyl-uracil.

6. The method of claim 1, wherein the bacterium is selected from the group consisting of the genus Pseudomonas, Flabobacterium, Achromobacter, Salmonella, Seratis, Aeromonas, Erwinia, Prateus, Bacterium, Xanthomonas, Klebsiella and Citrobacter.

7. The method of claim 1, wherein the bacterium belongs to the genus Escherichia.

8. The method of claim 1, wherein the bacterium belongs to the genus Enterobacter.

9. The method of claim 1, wherein the bacterium is selected from the group consisting of
Pseudomonas stutzeri NRRL B-11346,
Flavobacterium rhenanum NRRL B-11343,
Flavobacterium acidoficum ATCC 8366,
Flavobacterium proteus ATCC 12841,
Achromobacter lacticum NRRL B-11340,
Salmonella typhimirim NRRL B-11347,
Citrobacter freundii ATCC 98090,
Citrobacter freundii ATCC 6750,
Klebsiella pneumoniae ATCC 9621,
Serratia liquefaciens ATCC 14460,
Aeromonas punctata ATCC 11163,
Aeromonas salmonicida ATCC 14174,
Serratia marcescens IFO 3048,
Erwinia carotovora NRRL B-11342,
Erwinia amylovara NRRL B-11341,
Erwinia herbicola ATCC 14537,
Proteus vulgaris NRRL B-11345,
Proteus rettgeri NRRL B-11344,
Bacterium cadaveris IFO 3731, and
Xanthomonas citri NRRL B-11348.

10. The method of claim 1, wherein the bacterium is selected from the group consisting of Escherichia coli ATCC 9637, Escherichia aurescens ATCC 12814, and Enterobacter aerogenes ATCC 13048.

11. The method of claim 1, wherein the pH of the aqueous medium is from 4 to 10.

12. The method of claim 1, wherein cells of the bacterium are used as the enzyme.

* * * * *